US008788219B2

(12) United States Patent
Fingerhut et al.

(10) Patent No.: US 8,788,219 B2
(45) Date of Patent: Jul. 22, 2014

(54) METHOD OF DETERMINING AN EDGE OF AN ANOMALY, METHOD OF DETERMINING INTERACTION, METHOD OF ALIGNING, COMPUTER PROGRAM PRODUCT, AND DATA CARRIER

(75) Inventors: Martin Fingerhut, League City, TX (US); Deli Yu, Edmonton (CA)

(73) Assignee: Röntgen Technische Dienst B.V., Rotterdam (NL)

( * ) Notice: Subject to any disclaimer, the term of this patent is extended or adjusted under 35 U.S.C. 154(b) by 1046 days.

(21) Appl. No.: 12/778,081

(22) Filed: May 11, 2010

(65) Prior Publication Data

US 2011/0282592 A1 Nov. 17, 2011

(51) Int. Cl.
*G01B 5/28* (2006.01)

(52) U.S. Cl.
USPC .............................................. 702/38; 138/103

(58) Field of Classification Search
USPC .......................................................... 702/38
See application file for complete search history.

(56) References Cited

U.S. PATENT DOCUMENTS

| 8,156,812 | B2 * | 4/2012 | Tomar et al. | 73/602 |
|---|---|---|---|---|
| 8,316,712 | B2 * | 11/2012 | Muravin et al. | 73/587 |
| 2006/0100834 | A1 * | 5/2006 | Davis | 703/2 |
| 2006/0288756 | A1 | 12/2006 | De Meurechy | |
| 2009/0078049 | A1 * | 3/2009 | Sinha | 73/623 |
| 2009/0229362 | A1 * | 9/2009 | Tomar et al. | 73/592 |
| 2010/0131210 | A1 * | 5/2010 | Fingerhut et al. | 702/38 |
| 2011/0127999 | A1 * | 6/2011 | Lott et al. | 324/239 |
| 2011/0196621 | A1 * | 8/2011 | Huyse et al. | 702/34 |

FOREIGN PATENT DOCUMENTS

| WO | WO-2005/008223 | 1/2005 |
|---|---|---|
| WO | WO-2009/110795 | 9/2009 |

OTHER PUBLICATIONS

European Search Report for EP 11165697.1, mailed Oct. 13, 2011, 9 pages.
Palmer-Jones et al., "Getting more from your intelligent pig report assessing clusters", Pigging Products and Service Association (2007).
Ravan et al., "Sizing of multiple cracks using magnetic flux leakage measurements", IET Sci. Meas. Technol. (2010) 4(1):1-11.
Reber et al., "Run Comparisons: Using in-line Inspection Data for the Assessment of Pipelines", Pipeline Technology 2006 Conference (2006).
Manual for Determining the Remaining Strength of Corroded Pipelines, pp. 4-8, Oct. 30, 2009, The American Society of Mechanical Engineers.

(Continued)

*Primary Examiner* — Sujoy Kundu
*Assistant Examiner* — Alvaro Fortich
(74) *Attorney, Agent, or Firm* — Morrison & Foerster LLP

(57) ABSTRACT

Method of determining an edge of a first anomaly in a wall of a pipeline from a first set of data elements representing measurements of the wall of the pipeline. An element of the first set comprises a first coordinate, a second coordinate, and a parameter being indicative for the presence and/or severity of the first anomaly a position along the wall indicated by the first and second coordinate. The method comprises determining a data element that is associated with a maximum in the severity of the first anomaly; evaluating a value of the parameter by comparing with a predetermined threshold; determining an initial edge data element for which the parameter has reached the threshold; determining a next edge data element; determining further edge data elements; and determining the edge of the first anomaly by combining the first and second coordinates of the determined edge data elements.

39 Claims, 4 Drawing Sheets

(56) References Cited

OTHER PUBLICATIONS

A. Keith Escoe, Piping and Pipeline Assessment Guide, pp. 14-19, 2006, Elsevier.

Rafael C. Gonzalez et al., Digital Image Processing, 3rd Ed., pp. 630-634 and 815-817, 2008, Pearson Prentice Hall.

Milan Sonka et al., Image Processing, Analysis, and Machine Vision, 3rd Ed., pp. 175-176, 191-193, and 242, 2008, Thomson.

John C. Russ, The Image Processing Handbook, pp. 265-269, 1992, CRC Press.

Gary Bradski et al., Learning OpenCV, pp. 1-2 and 234-262, 2008, O'Reilly Media.

Satoshi Suzuki et al., Topological Structural Analysis of Digitized Binary Images by Border Following, pp. 32-46, 1985.

\* cited by examiner

METHOD OF DETERMINING AN EDGE OF AN ANOMALY, METHOD OF DETERMINING INTERACTION, METHOD OF ALIGNING, COMPUTER PROGRAM PRODUCT, AND DATA CARRIER

The invention relates to a method of determining an extent of a first anomaly in a wall of a pipeline from a first set of data elements representing measurements of the wall of the pipeline. The invention also relates to a method of determining whether anomalies in a wall of a pipeline interact. The invention also relates to method of aligning a first set of measured data elements with a second set of measured data elements, wherein at least a part of the first set of measured data elements and at least a part of the second set of measured data elements are acquired from one and the same portion of the wall of the pipeline. The invention also relates to a computer program product and a data carrier.

In-line inspection (ILI) is a popular method of inspecting buried pipelines for anomalies in a wall of the pipelines. Such pipelines are e.g. used for transporting liquids and natural gas therethrough. Said inspection can be performed by launching an in-line-inspection tool (also referred to as a 'pig') fitted with measurement sensors, e.g. magnetic flux leakage (MFL) sensors, ultrasonic measurement sensors, or electromagnetic acoustic transducers, that perform measurements as the tool travels through the pipeline. The measurements may then be analysed and interpreted to determine the condition of the pipeline, so that pipeline operators can devise a mitigation and/or repair plan to maintain safe operation of the pipeline.

MFL measurements are used in many in-line inspections due to their broad applicability. While MFL measurements may provide valuable information, these measurements however may be relatively vulnerable to various factors that may affect the accuracy and reliability of these measurements. As a result, MFL measurements inherently have some error which has to be taken into account to ensure a proper mitigation and/or repair plan.

Errors in MFL measurements can have various causes, being systemic and/or random. The MFL data are e.g. dependent on a geometry (length, depth, width, morphology) of an anomaly in the pipe, so that e.g. anomalies having a mutually different geometry but posing a comparable risk to the pipeline may not be recognised as being comparable. Furthermore, random errors may be caused by e.g. variations in tool speed when it travels through the pipeline, sensor lift-off from the wall of the pipeline, localized hard-spots in the wall of the pipeline, heat affected zones at weld locations of the pipeline, and changes in material properties of the wall of the pipeline.

While it is difficult to eliminate these errors, the MFL measurements can still be used in a fruitful and fiduciary manner by engineers by incorporating and accounting for these errors in their risk assessment and planning. Typically however, in known methods these errors are accounted for in the same way for all anomalies, based on idealized anomaly assumptions. As a result, such known methods account for the errors rather broadly and conservatively, thereby forcing conservatism in the mitigation and/or repair plans.

It is therefore an object of the invention to enable improved data analysis for inspecting a wall of a pipeline.

Thereto the invention provides a method of determining an edge of a first anomaly in a wall of a pipeline from a first set of data elements representing measurements of the wall of the pipeline, an element of the first set comprising a first coordinate along a first direction along the wall, a second coordinate along a second direction along the wall that is different from the first direction, and a parameter, in particular a third coordinate in a third direction transverse to first and second direction, the parameter being indicative for the presence and/or severity of the first anomaly, in particular for a depth of the first anomaly, at a position along the wall indicated by the first and second coordinate, the method comprising the steps: a) determining, by evaluating the parameters of the data elements, a data element that is associated with the first anomaly and/or a maximum in the severity of the first anomaly, and preferably is associated with a minimum or a maximum in a value of the parameter; b) evaluating, for at least one data element present on a path along the wall which extends away from the data element found in step a), a value of the parameter by comparing the value of the parameter with a predetermined threshold; c) determining an initial edge data element for which, during evaluating in step b), the parameter has reached the threshold; d) determining, by evaluating the parameter of at least one data element that is adjacent, in particular neighbouring, to the initial edge data element determined in step c), a next edge data element that is different from the initial edge data element determined in step c) and for which the value of the parameter has reached the threshold; e) determining further edge data elements by repeating step d) a plurality of times wherein the next edge data element that is determined in a step d) is different from previously determined edge data elements; and f) determining the edge of the first anomaly by combining the first and second coordinates of the edge data elements determined in steps c)-e). In this way, the edge of the first anomaly can be determined with relatively high accuracy. Such information on the edge of the first anomaly can e.g. be used for comparison with a second set of measured data elements (a second data set), e.g. an MFL data set, obtained by in-line inspection. As a result, the magnitude and source of errors in the second data set can be identified relatively reliably by comparison with the first set of measured data elements (the first data set) that may have a relatively high accuracy. As a result, pipeline operators can better account for errors in the second data set, as measured. Hence, improved data analysis for inspecting the wall of the pipeline may be enabled. In this way mitigation and/or repair plans may be improved, in particular unnecessary repair costs may be prevented. It may thus be enabled that mitigation and/or repair plans based on MFL-data can be less conservative.

The term 'anomaly' is used herein to refer to a broad range of defects. A crack in the wall, a cavity in the wall, and corrosion of the wall are all regarded as anomalies in the wall. The terms 'measurements', 'measured data elements' and the like may refer to raw measured data but also to processed data that are based on the raw measured data. The data element that is associated with a maximum, e.g. a local maximum, in the severity of the first anomaly may e.g. be located at or adjacent to a position of the maximum in the severity of the first anomaly. The data element that is associated with the maximum in the severity of the first anomaly may optionally be formed by any data element of the first anomaly having a value of the parameter being lower than the threshold preferably by a predetermined amount, e.g. if the maximum in the severity of the first anomaly is associated with a minimum in the value of the parameter. Alternatively the data element that is associated with the maximum in the severity of the first anomaly may optionally be formed by any data element of the first anomaly having a value of the parameter being higher than the threshold preferably by a predetermined amount, e.g. if the maximum in the severity of the first anomaly is associated with a maximum in the value of the parameter. The maximum in the severity of the first anomaly may optionally be a local maximum. This means that the maximum in the severity of the first anomaly may optionally be smaller than a severity of another anomaly or may optionally be smaller than a severity elsewhere in the first anomaly. Similarly, the minimum in the value of the parameter may optionally be a local minimum. Similarly, the maximum in the value of the parameter may optionally be a local maximum.

In an embodiment, the maximum in the severity of the first anomaly is associated with a minimum in the value of the parameter that is smaller than the threshold. In another embodiment, the maximum in the severity of the first anomaly is associated with a maximum in the value of the parameter that is larger than the threshold.

Preferably, the edge of the first anomaly determined in step f) forms an edge path around the data element that is associated with the maximum in the severity of the first anomaly.

In an embodiment, the edge path encloses anomaly data elements. Preferably, if the maximum in the severity of the first anomaly is associated with the minimum in the value of the parameter, the anomaly data elements have a value of the parameter that is smaller than the threshold. Preferably, if the maximum in the severity of the first anomaly is associated with the maximum in the value of the parameter, the anomaly data elements have a value of the parameter that is larger than the threshold.

Preferably, step e) is repeated until one of the further edge data elements is adjacent, in particular neighbouring, to the initial edge data element determined in step c). In this way, the edge can be determined rather completely. However, the invention may also be valuable when only a part of the edge is determined.

Preferably, the path along the wall extends in a direction parallel with the first direction or the second direction. This enables a convenient way of determining the initial edge data element.

In an embodiment, the method further comprises the step: g) defining a base edge envelope of the first anomaly that preferably extends via data elements of the first set, more preferably via at least one of the edge data elements of the first anomaly, and that encloses the edge of the first anomaly. Using such a base edge envelope enables standardisation of properties of the first anomaly. For example, the base edge envelope preferably has a width, a length, a position along the wall of the pipeline, and/or is associated with a depth in the wall of the pipeline. The depth associated with the edge envelope may optionally be dependent on a depth of the anomaly associated with that edge envelope. Optionally, the depth associated with said edge envelope may e.g. be set proportional to, in particular equal to, a maximum depth of the anomaly associated with that edge envelope. For example, the position and/or the depth along the wall of the pipeline of the edge envelope of the first anomaly may be determined by respectively the first and second coordinate, and/or the parameter, of the data element that is associated with the maximum in the severity of the first anomaly. In this way the first anomaly can be compared with other anomalies by comparing the base edge envelope with other envelopes of the other anomalies. Preferably, the base edge envelope of the first anomaly is box-shaped, i.e. has a rectangular shape. Box-shaped edge envelopes enable a relatively straightforward and also relatively accurate standardisation of anomaly properties such as width and length.

In an embodiment, the method comprises the steps: h) repeating steps a)-f) for determining an edge of a second anomaly that is different from the first anomaly; i) determining, based on the edge of the first anomaly and the edge of the second anomaly, and by using an interaction criterium, whether the first anomaly and the second anomaly interact. Recognising such interaction is important, as otherwise a condition of the pipeline would be assessed too optimistically.

In an embodiment, determining in step i) is based on the base edge envelope of the first anomaly and the edge of the second anomaly. Preferably, the method comprises the step: j) defining a base edge envelope of the second anomaly that preferably extends via data elements of the first set, more preferably via at least one of the edge data elements of the second anomaly, and that encloses the edge of the second anomaly, wherein determining in step i) is based on the base edge envelope of the first anomaly and the base edge envelope of the second anomaly. Such a base edge envelope of the second anomaly may preferably be determined analogously to determining the base edge envelope of the first anomaly. Determining interaction between the first anomaly and the second anomaly by using the base edge envelopes facilitates applying interaction criteria in a standardised way. Preferably, the interaction criterium is dependent on, e.g. takes into account, the depth of edge envelopes, e.g. the first and/or the second base edge envelope. Preferably, the base edge envelope of the second anomaly is box-shaped, i.e. has a rectangular shape. Box-shaped edge envelopes may have a width and a length which may be used in interaction criteria.

In an embodiment, determining in step i) whether the first anomaly and the second anomaly interact by using the interaction criterium comprises enlarging the base edge envelope of the first anomaly to obtain an enlarged base edge envelope and further comprises determining whether the enlarged base edge envelope overlaps, overlays and/or crosses the base edge envelope of the second anomaly.

In an embodiment, a step k) is carried out if in step i) it is determined that the first anomaly and the second anomaly interact, wherein step k) comprises: defining an interaction edge envelope that preferably extends via data elements of the first set, more preferably via at least one of the edge data elements of the first and second anomaly, and that encloses the edge of the first and the second anomaly.

In an embodiment, the method comprises the steps: l) repeating steps a)-f) for defining an edge of a third anomaly that is different from the first anomaly and the second anomaly; and m) determining, based on the edge of the first anomaly, the edge of the second anomaly, and the edge of the third anomaly, and by using an interaction criterium, whether the first anomaly and/or the second anomaly interact with the third anomaly.

In an embodiment, determining in step m) is based on the interaction edge envelope and the edge of the third anomaly. Preferably, the method comprises the step: n) defining a base edge envelope of the third anomaly that preferably extends via data elements of the first set, more preferably via at least one of the edge data elements of the third anomaly, and that encloses the edge of the third anomaly, wherein determining in step m) is based on the interaction edge envelope and the base edge envelope of the third anomaly. Determining interaction between anomalies by using the edge envelopes facilitates applying interaction criteria in a standardised way. Preferably, the base edge envelope of the third anomaly is box-shaped, i.e. has a rectangular shape.

In an embodiment, determining in step m) whether the first anomaly and/or the second anomaly interact with the third anomaly by using the interaction criterium comprises enlarging the interaction edge envelope to obtain an enlarged interaction edge envelope and further comprises determining whether the interaction edge envelope overlaps, overlays and/or crosses the base edge envelope of the third anomaly.

Preferably, the first set of measured data element is acquired by means of laser profilometry. Preferably, the first anomaly, the second anomaly, and/or the third anomaly are located on an inner or outer surface of the wall of the pipeline. This may enable measurement of a depth of the anomalies by means of laser profilometry.

In an embodiment, the method comprises aligning the first set of measured data elements with a second set of measured data elements, wherein at least a part of the first set of measured data elements and at least a part of the second set of measured data elements are acquired from one and the same portion of the wall of the pipeline, the method comprising the steps: o) defining a plurality of edge envelopes of the anomalies of the first set of measured data elements associated with the portion of the wall of the pipeline, which are defined similarly to defining the edge envelope of the first anomaly; p) defining a plurality of edge envelopes of the anomalies of the second set of measured data elements associated with the portion of the wall of the pipeline; q) comparing the plurality of the edge envelopes of the anomalies of the first set of measured data elements with the plurality of the edge envelopes of the anomalies of the second set of measured data elements; and r) adapting the edge envelopes of the second set of measured data elements, based on the comparing of step q). Such adapting enables improvement of the second data set, and thus enables improved data analysis for inspecting the wall of the pipeline. The features of this embodiment may be implied independently, meaning that the plurality of edge envelopes of the anomalies of the first set of measured data element associated with the portion of the wall of the pipeline do not necessarily have to be defined similar to defining the edge envelope of the first anomaly.

In an embodiment, adapting in step r) comprises shifting a position of the edge envelopes of the second set of measured data elements. In this way, a position measurement of the anomalies of the second set of measured data elements may be improved.

In an embodiment, adapting in step r) includes redefining and/or reclustering the edge envelopes of the anomalies of the first set of measured data elements and/or the second set of measured data elements. In this way, the application of interaction criteria and/or the assessment of the condition of the pipeline may be improved.

In an embodiment, comparing edge envelopes in step q) comprises comparing at least one of a width of the edge envelope, a length of the edge envelope, a position of the edge envelop, and a depth associated with the edge envelopes. In this way, correlation of the first data set and the second data set may be improved.

In an embodiment, the first and/or second set of measured data elements is acquired by means of an in-line inspection method of the pipeline.

In an embodiment, the second set of measured data elements is acquired by means of a magnetic flux leakage (MFL) inspection, by ultrasonic inspection, and/or by electromagnetic-acoustic inspection of the pipeline.

In an embodiment, the threshold has a predetermined value, e.g. dependent of the measurement method with which the first set of measured data elements was acquired. However, alternatively, the threshold may be dependent on values of one or more of the parameters of data elements of the first set of measured data elements. For example, the threshold used for determining the edge of the first anomaly may be set equal to a predetermined fraction of the minimum or the maximum of the value of the parameter of the data element that is associated with the maximum in the severity of the first anomaly. As another example, the threshold may have a predetermined difference with the minimum or the maximum of the value of the parameter of the data element that is associated with the maximum in the severity of the first anomaly. Optionally, the threshold may be similar for a plurality of anomalies similar to the first anomaly. The threshold may e.g. be set equal to a predetermined fraction of an average value of the parameters of the first set of measured data. Alternatively, the threshold may have a predetermined difference with the average value of the parameters of the first set of measured data.

The invention also provides a method of determining whether a first anomaly and a second anomaly in a wall of a pipeline interact, based on edges of the first and second anomaly that are determined from a first set of measured data elements representing measurements of the wall of the pipeline, an element of the first set preferably comprising a first coordinate along a first direction along the wall, a second coordinate along a second direction along the wall that is different from the first direction, and a parameter, in particular a third coordinate in a third direction transverse to first and second direction, the parameter being indicative for the presence and/or severity of the first or second anomaly, in particular for a depth of the first or second anomaly, at a position along the wall indicated by the first and second coordinate, the edges enclosing anomaly data elements associated with the first or second anomaly for which a value of the parameter preferably has crossed a threshold value, the method comprising the steps: s) providing a base edge envelope of the first anomaly that encloses the edge of the first anomaly, wherein the base edge envelope of the first anomaly preferably is box-shaped; t) providing a base edge envelope of the second anomaly that encloses the edge of the second anomaly, wherein the base edge envelope of the second anomaly preferably is box-shaped; u) determining, based on the base edge envelope of the first anomaly and the base edge envelope of the second anomaly, and by using an interaction criterium, whether the first anomaly and the second anomaly interact. Using edge envelopes enables standardisation of properties of anomalies. Determining interaction between the first anomaly and the second anomaly by using the base edge envelopes facilitates applying interaction criteria in a standardised way. Hence, improved data analysis for inspecting the wall of the pipeline may be enabled. Preferably, the base edge envelope of the first and/or the second anomaly is box-shaped. Box-shaped edge envelopes may have a width and a length which may be used in interaction criteria.

The parameter having crossed the threshold value may mean that the parameter is smaller than the threshold value, if the maximum in the severity of the first anomaly is associated with a minimum in the value of the parameter that is smaller than the threshold value. Alternatively, the parameter having crossed the threshold value may mean that the parameter is larger than the threshold value, if the maximum in the severity of the first anomaly is associated with a maximum in the value of the parameter that is larger than the threshold value.

Preferably, the edge of the first anomaly forms an edge path around the anomaly data elements of the first anomaly and/or the edge of the second anomaly forms an edge path around the anomaly data elements of the second anomaly.

Preferably, determining in step u) whether the first anomaly and the second anomaly interact by using the interaction criterium comprises enlarging the edge envelope of the first anomaly to obtain an enlarged edge envelope and further comprises determining whether the enlarged edge envelope overlaps, overlays and/or crosses the edge envelope of the second anomaly.

Preferably, steps t)-u) are repeated a plurality of times for a number of different first and second anomalies. The method may be carried out by using, e.g. during a number of the repetitions, instead of the base edge envelope of the first and/or second anomaly, an interaction edge envelope and/or a further interaction edge envelope, which may enclose respectively two or more than two base edge envelopes.

The invention also provides a method of aligning a first set of measured data elements with a second set of measured data elements, the first and second set of measured data elements representing measurements of the wall of the pipeline, an element of the first or second set preferably comprising a first coordinate along a first direction along the wall, a second coordinate along a second direction along the wall that is different from the first direction, and a parameter, in particular a third coordinate in a third direction transverse to first and second direction, the parameter being indicative for the presence and/or severity of an anomaly, in particular for a depth of the anomaly, at a position along the wall indicated by the first and second coordinate, wherein at least a part of the first set of measured data elements and at least a part of the second set of measured data elements are acquired from one and the same portion of the wall of the pipeline, wherein edges of anomalies are provided that are determined from the first and second set of measured data elements, the edges enclosing anomaly data elements for which preferably a value of the parameter has crossed a threshold value, the method comprising the steps: v) providing a plurality of edge envelopes of the anomalies of the first set of measured data element associated with the portion of the wall of the pipeline; w) providing a plurality of edge envelopes of the anomalies of the second set of measured data elements associated with the portion of the wall of the pipeline; x) comparing the plurality of the edge envelopes of the anomalies of the first set of measured data elements with the plurality of the edge envelopes of the anomalies of the second set of measured data elements; and y) adapting the edge envelopes of the second set of measured data elements, based on the comparing of step x). Such adapting enables improvement of the second data set, and thus enables improved data analysis for inspecting the wall of the pipeline.

Preferably, adapting in step y) comprises shifting a position of the edge envelopes of the second set of measured data elements. Preferably, adapting in step y) includes redefining the edge envelopes of the anomalies of the second set of measured data elements. Preferably, comparing edge envelopes in step q) comprises comparing at least one of a width of the edge envelopes, a length of the edge envelopes, a position of the edge envelopes, and a depth associated with the edge envelopes.

Preferably, the first and/or second set of measured data elements is acquired by means of an in-line inspection method of the pipeline. Preferably, the first set of measured data elements is acquired by means of laser profilometry. Preferably, the second set of measured data elements is acquired by means of a magnetic flux leakage (MFL) inspection, by ultrasonic inspection, and/or by electromagnetic-acoustic inspection of the pipeline. Preferably, the anomalies are located on an inner or outer surface of the wall of the pipeline.

The parameter having crossed the threshold value may mean that the parameter is smaller than the threshold value, if the maximum in the severity of the first anomaly is associated with a minimum in the value of the parameter that is smaller than the threshold value. Alternatively, the parameter having crossed the threshold value may mean that the parameter is larger than the threshold value, if the maximum in the severity of the first anomaly is associated with a maximum in the value of the parameter that is larger than the threshold value.

The invention also provides a computer program product including computer code portions arranged for performing, when run on a programmable apparatus, the steps of a method according to the invention.

The computer program product may e.g. be arranged for carrying out a method of determining an edge of a first anomaly in a wall of a pipeline from a first set of data elements representing measurements of the wall of the pipeline, an element of the first set comprising a first coordinate along a first direction along the wall, a second coordinate along a second direction along the wall that is different from the first direction, and a parameter, in particular a third coordinate in a third direction transverse to first and second direction, the parameter being indicative for the presence and/or severity of the first anomaly, in particular for a depth of the first anomaly, at a position along the wall indicated by the first and second coordinate, the method comprising the steps: a) determining, by evaluating the parameters of the data elements, a data element that is associated with a maximum in the severity of the first anomaly; b) evaluating, for at least one data element present on a path along the wall which extends away from the data element found in step a), a value of the parameter by comparing the value of the parameter with a predetermined threshold; c) determining an initial edge data element for which, during evaluating in step b), the parameter has reached the threshold; d) determining, by evaluating the parameter of at least one data element that is adjacent, in particular neighbouring, to the initial edge data element determined in step c), a next edge data element that is different from the initial edge data element determined in step c) and for which the value of the parameter has reached the threshold; e) determining further edge data elements by repeating step d) a plurality of times wherein the next edge data element that is determined in a step d) is different from previously determined edge data elements; and f) determining the edge of the first anomaly by combining the first and second coordinates of the edge data elements determined in steps c)-e).

The invention also provides a data carrier including the computer program product. Herein the data carrier may for instance comprise a magnetic data carrier, such as a hard disk, an optical data carrier, such as a compact disk (CD) or DVD, or a solid state device data carrier, or carrier waves, such as available on an intranet or the internet.

The invention will now be illustrated, in a non-limiting way, with reference to the accompanying drawing, wherein.

Unless stated otherwise, like reference numerals refer to like elements throughout the drawings.

Figure 1:
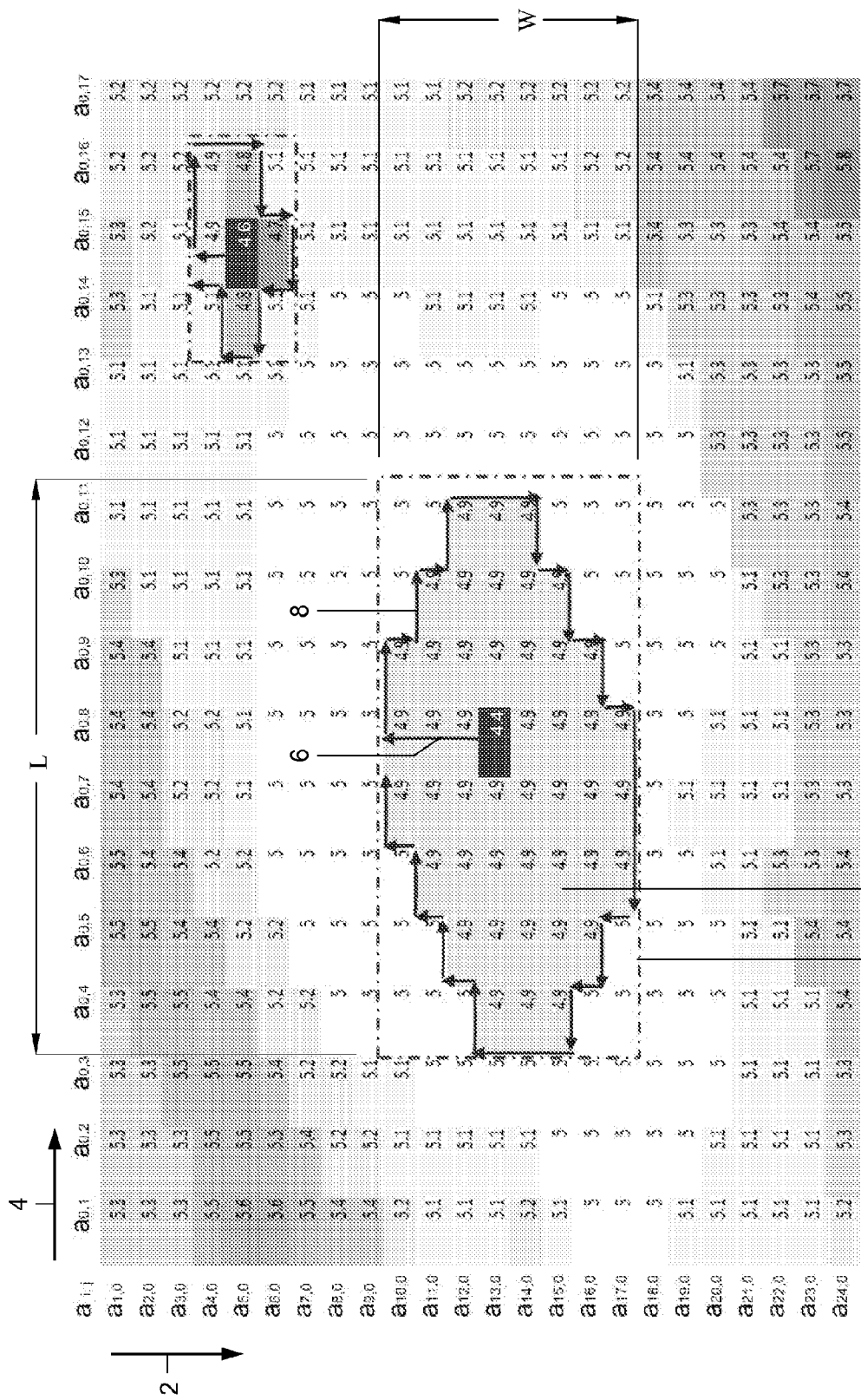
FIG. 1 shows a first set of data elements representing measurements of a wall of a pipeline.

FIG. 1 shows a first set of data elements $a_{i,j}$ representing measurements of a wall of a pipeline, in this example a pipeline that can be used for transporting liquids and natural gas. Index i represents a first coordinate along a first direction along the wall. Index j represents a second coordinate along a second direction along the wall. The first direction 2 is different from the second direction 4, and is for example orthogonal to the second direction 4. The first direction may 2 coincide with a circumferential of the pipeline. The second direction 4 may coincide with a longitudinal, also called axial, direction of the pipeline. In this example the wall of the pipeline may generally be ring-shaped when seen in a cross-section of the pipeline that is made perpendicular to the longitudinal direction. Thus, an inner and/or outer surface of the wall of the pipeline may be of cylindrical shape.

In addition to the first coordinate i and the second coordinate j, the data elements $a_{i,j}$ may comprise a parameter, in particular a third coordinate in a third direction transverse to first and second direction. In the example of FIG. 1, the parameter is indicated by a number. For example, the parameter of the data element $a_{1,1}$ equals 5.3, and the parameter of the data element $a_{8,4}$ equals 5. The parameter is indicative for the presence and/or severity of a first anomaly 10 in the wall of the pipeline, in particular for a depth of the first anomaly 10, at a position along the wall of the pipeline indicated by the first and second coordinate i,j.

A first embodiment of a method according to the invention (the first method) may comprise evaluating the parameters of the data elements $a_{i,j}$. As a result of such evaluating, a data element $a_{i,j}$ may be determined that is associated with a maximum in the severity of the first anomaly 10. In the example of FIG. 1, the data element $a_{13,8}$ can be associated with the maximum of the severity of the first anomaly 10. FIG. 1 shows that the data element $a_{13,8}$ has a parameter having a value equal to 4.4, which is smaller than all other data element $a_{i,j}$, (i=1, ..., 14, j=1, ..., 17) in this example.

A path 6 may be defined along the wall which extends away from the data element $a_{13,8}$ having the maximum in the severity of the first anomaly 10. In this example, the path 6 along the wall is parallel with the first direction 2. The first method may comprise evaluating, for data elements present on the path 6, a value of the parameter by comparing the value of the parameter with a predetermined threshold. In the example of FIG. 1, the threshold equals 4.95. The first method may comprise determining an initial edge data element for which, during evaluating, the parameter has reached the threshold of 4.95. The term 'reaching' should be interpreted broadly and may mean 'exceeding' or 'coming within a predetermined distance from'. Hence, along the path 6, the threshold of 4.95 is reached for example at data element $a_{10,8}$, where the parameter comes within a predetermined distance of 0.5 from the threshold. Alternatively, the threshold 4.95 can be regarded to be reached at data element $a_{9,8}$ where it is first exceeded.

Thus, in the example of FIG. 5, the initial edge data element is the data element $a_{10,8}$ on the path 6. After having determined the initial edge data element $a_{10,8}$, the first method may comprise determining a next edge data element $a_{10,9}$ that is different from the initial edge data element. Such determining may be carried out by evaluating the parameter of data elements that are adjacent, in particular neighbouring, to the initial edge data element $a_{10,8}$. In the example of FIG. 1, data elements $a_{9,8}$, $a_{11,8}$, $a_{10,9}$, and $a_{10,7}$ are neighbouring, i.e. are directly adjacent to, the initial edge data element $a_{10,8}$. Also data elements $a_{9,9}$, $a_{11,9}$, $a_{11,7}$, and $a_{9,7}$ may be considered as neighbouring data elements. By comparing the parameter with the threshold, it may be determined for which one of the neighbouring data element the parameter has reached the threshold. Based on such comparing, the next edge data element may be selected. More in general, determining the next edge data element may be carried out after comparing the parameters of the neighbouring data elements of the initial edge data element with the threshold one by one in a predetermined order, e.g. in a clockwise fashion, e.g. starting from the data element that is neighbouring to the initial edge data element along the path 6 in a direction away from the first anomaly 10. The first data element where the threshold is reached may be selected, here data element $a_{10,9}$.

The first method may comprise determining further edge data elements. This can be carried out analogously to determining the next data element from the neighbouring data element of the initial edge data element. Thus, the first method may comprise repeating a plurality of times method steps carried out steps for determining the next edge data element. Such further edge data elements are different from previously determined edge data elements. Further edge data elements may be determined until a further data element is adjacent, in particular neighbouring, to the initial edge data element. For example in this way the edge 8, in particular a position of the edge 8, of the first anomaly 10 can be determined by combining the first and second coordinates i,j of the edge data elements $a_{i,j}$ determined in the first method. Hence, the edge 8 of the first anomaly forms an edge path around the data element $a_{13,8}$ that is associated with the maximum in the severity of the first anomaly. The edge path encloses anomaly data elements, e.g. the data element $a_{13,8}$ that is associated with the maximum in the severity of the first anomaly.

The maximum in the severity of the first anomaly may be associated with a minimum in the value of the parameter that is smaller than the threshold, as in the example of FIG. 1. Alternatively the maximum in the severity of the first anomaly may be associated with a maximum in the value of the parameter that is larger than the threshold. If the maximum in the severity of the first anomaly is associated with the minimum in the value of the parameter the anomaly data elements may have a value of the parameter that is smaller than the threshold. If the maximum in the severity of the first anomaly is associated with the maximum in the value of the parameter the anomaly data elements may have a value of the parameter that is larger than the threshold.

In a second embodiment of a method according to the invention (the second method), the first method can be further extended. The second method may comprise defining a base edge envelope 12A of the first anomaly 10 that encloses the edge of the first anomaly 10. The base edge envelope 12A may extend via data elements of the first set. This means that the base edge envelope 12A may be formed by first and second coordinates of data elements $a_{i,j}$ of the first set. Preferably, the base edge envelope 12 extends via at least one of the edge data elements of the first anomaly 10. This means that preferably the base edge envelope 12A and the edge data elements of the first anomaly 10 have at least on pair of a first coordinate and a second coordinate in common. Also in this case, the base edge envelope 12A is considered to enclose the edge of the first anomaly 10.

Figure 2:
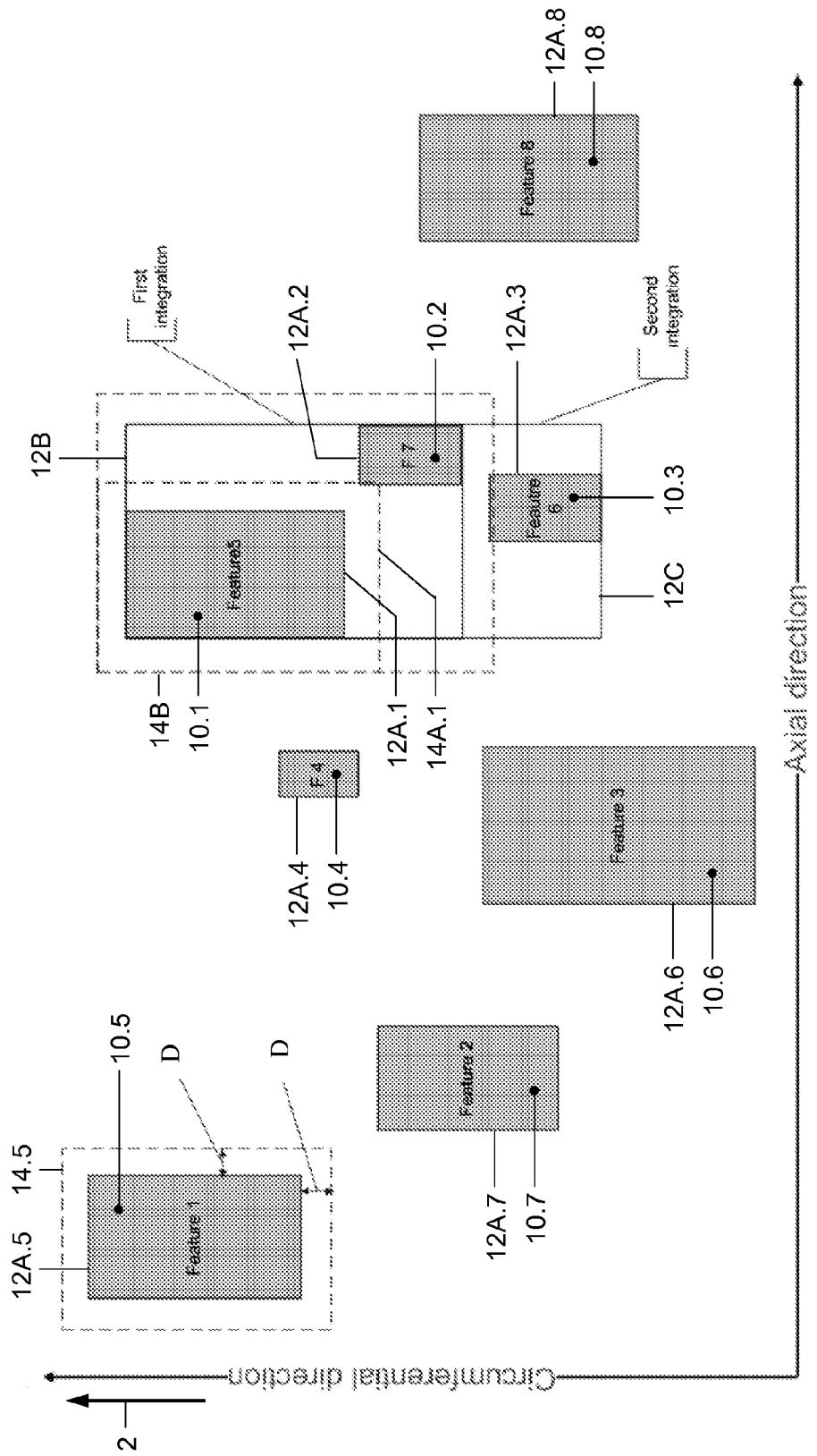
FIG. 2 illustrates a second method.

The second method is further illustrated with reference to FIG. 2, which shows eight base edge envelopes 12A.k respectively enclosing eight anomalies 10.k (k=1, ..., 8). An anomalies 10.k may also be referred to as feature k (FIG. 2). The first anomaly is referred to with reference number 10.1. A second anomaly is referred to with reference number 10.2. A third anomaly is referred to with reference number 10.3, etc. The first, in this example circumferential, direction 2 and the second, in this example longitudinal, direction 4 are also indicated in FIG. 2. In the example of FIG. 2, the base edge envelopes 12A.k are box-shaped.

In FIG. 2 eight base edge envelopes 12A.k are defined. Defining the base edge envelopes 12A.k of FIG. 2 may comprise repeating the steps of the first method for each anomaly 10.k.

The second method may comprise determining, based on the base edge envelope 12A.1 of the first anomaly 10.1 and the base edge envelope 12A.2 of the second anomaly 10.2, and by using an interaction criterium, whether the first anomaly 10.1 and the second anomaly 10.2 interact. Determining whether the first and second anomaly 10.1, 10.2 interact may, more in general, comprise enlarging the base edge envelope 12A.1 to obtain an enlarged base edge envelope 14A.1. Such determining may further comprise determining whether the enlarged base edge envelope 14A.1 overlaps, overlays and/or crosses the base edge envelope 12A.2 of the second anomaly. If such overlap, overlay and/or crossing exists, it may be decided that the first anomaly and the second anomaly interact. Such deciding may be carried out automatically. It may be clear however that determining whether the first and second anomaly interact may also be performed based on the edge 8 of the first anomaly and an edge of the second anomaly. Alternatively, determining whether the first and second anomaly 10.1, 10.2 interact may be performed based on the edge 8 of the first anomaly and the base edge envelope 12A.2 of the second anomaly.

The enlargement of the first base edge envelope 12A.1 to obtain the enlarged base edge envelope 14A.1 may be based on an interaction criterium. A distance of such enlarging D may e.g. be a fixed distance. Alternatively, the distance of enlargement D may e.g. be proportional to a square root of a dimension of the base edge envelope, for example a width W or a length L of the base edge envelope (FIG. 1). The distance of enlargement D in the first direction may be equal or different to the distance of enlargement D in the second direction. It may thus be appreciated that various interaction criteria can be used. Such interaction criteria may as such be known to the skilled person so that a further description is deemed superfluous.

Hence, the second method may comprise determining that the first anomaly 10.1 and the second anomaly 10.2 interact. Then, in the case of interaction between the first and second anomaly 10.1, 10.2, the second method may further comprise defining an interaction edge envelope 12A that encloses the edge of the first anomaly 10.1 and the edge of the second anomaly 10.2. The interaction edge envelope 12B may replace the base edge envelopes 12A.1, 12A.2 of the first and second anomaly. In this way the base edge envelopes 12A.1, 12A.2 may be reclustered into the interaction edge envelope 12B. More in general, the interaction edge envelope 12B may be box-shaped. The interaction edge envelope 12B may extend via data elements of the first set, preferably via at least one of the edge data elements of the first and second anomaly. As in the example of FIG. 2, the interaction edge envelope 12B may, more in general, partly coincide with the base edge envelope 12A.1 and the base edge envelope 12A.2 of respectively the first anomaly 10.1 and the second anomaly 10.2.

The second method may further comprise determining whether the first anomaly and/or the second anomaly 10.1, 10.2 interact with the third anomaly 10.3. This may be carried out analogously with determining whether the first and second anomaly interact, however with a difference in that the interaction edge envelope 12B is used instead of the base edge envelope 12A.1 of the first anomaly 10.1, and the base edge envelope 12A.3 of the third anomaly 10.3 is used instead of the base edge envelope 12A.2 of the second anomaly 10.2. Hence, determining whether the first and/or second anomaly interact with the third anomaly may, more in general, comprise enlarging the interaction edge envelope 12B to obtain an enlarged interaction envelope 14B. Determining whether such interaction exists may further comprise determining whether the enlarged interaction envelope 14B overlaps, overlays and/or crosses the base edge envelope 12A.3 of the third anomaly 10.3. If such overlap, overlay and/or crossing exists, it may be decided that the first anomaly 10.1 and/or the second anomaly 10.2 interact with the third anomaly 10.3. Such deciding may be carried out automatically, e.g. by means of a computer. In case of such interaction, the second method may further comprise defining a further interaction edge envelope 12C that encloses the edge of the first, second, and third anomaly. More in general, the further interaction edge envelope 12C may be box-shaped. The further interaction edge envelope 12C may extend via data elements of the first set, preferably via at least one of the edge data elements of the first and second anomaly. As in the example of FIG. 2, the further interaction edge envelope 12C may, more in general, partly coincide with the interaction edge envelope 12B and the third base edge envelope 12A.3. It may thus be clear that the second method may comprise determining, based on the edge of the first anomaly and the edge of the second anomaly, in particular based on the interaction edge envelope 12B, and the edge of the third anomaly, in particular based on the edge envelope 12A.3 of the third anomaly, and by using an interaction criterium, whether the first anomaly and/or the second anomaly interact with the third anomaly.

Figure 3:
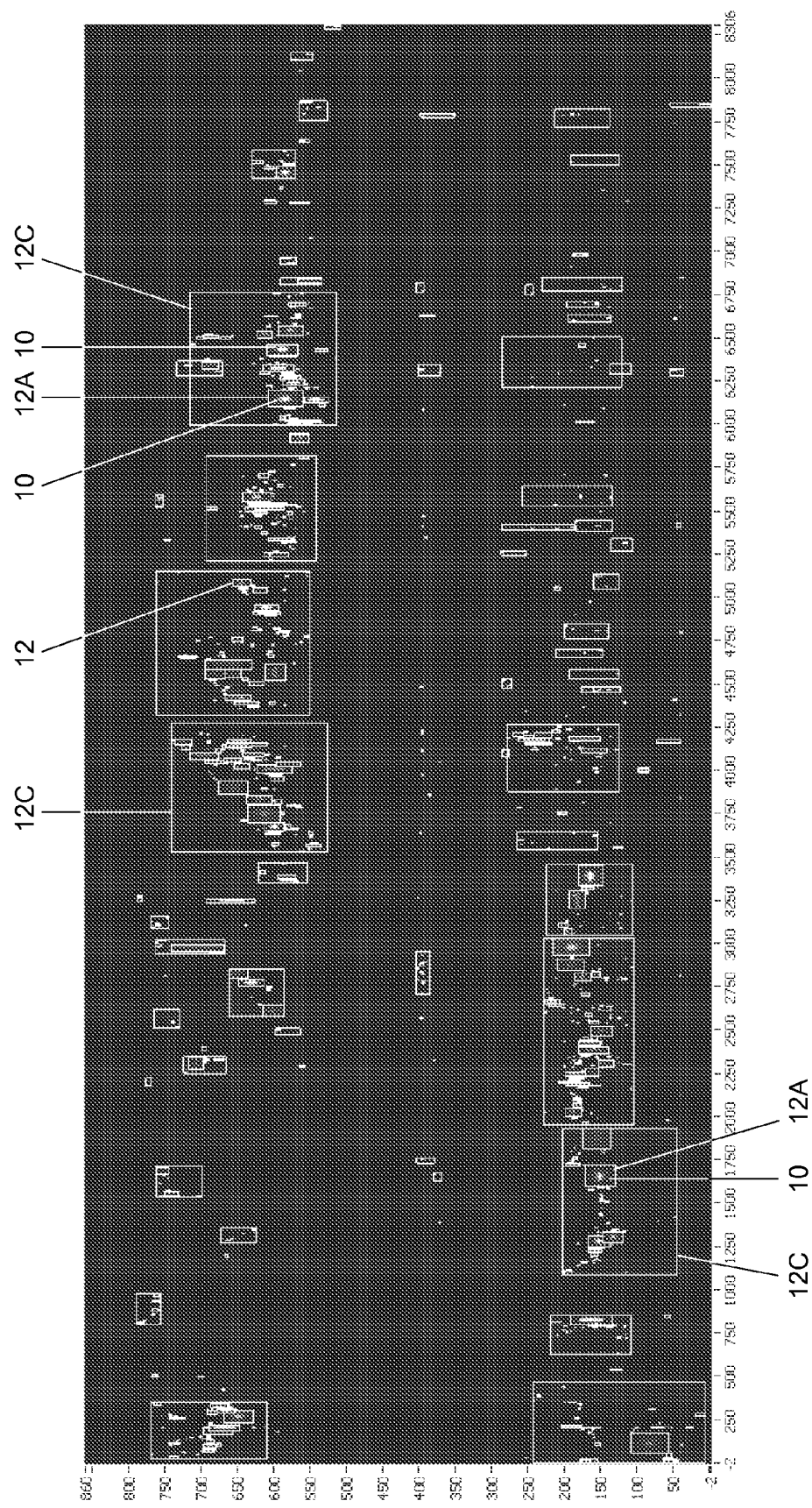
FIG. 3 shows an example of anomalies acquired by laser profilometry.

In e.g. the first and/or second method, the first set of measured data elements may have been acquired by means of laser profilometry. FIG. 3 shows an example of anomalies 10 acquired by laser profilometry, represented by e.g. box-shaped base edge envelopes 12A and further interaction edge envelopes 12C. By using laser profilometry, a relatively small error can be achieved when measuring the depth of anomalies 10. Laser profilometry may provide enough details to allow comparison with one or more other data sets being acquired from at least a portion of the wall of the pipeline from which at least a portion of the first set of measured data elements was acquired. Thus, at least a part of the first set of measured data elements and at least a part of the second set of measured data elements are acquired from one and the same portion of the wall of the pipeline. Instead of being acquired by laser profilometry, the first set of measured data elements may be required by excavation of the pipeline and carrying out manual measurements. However, this method, like many manual processes, is susceptible to significant errors.

A third embodiment of a method according to the invention (the third method) may comprise aligning the first set of measured data elements with a second set of measured data elements. The first set of measured data elements may be acquired by using a relatively accurate measurement method such as laser profilometry, on a relatively small part of the inner surface of the wall of the pipeline. Alternatively or additionally, the first set of measured data elements may be acquired by using a relatively accurate measurement method such as laser profilometry, on a relatively small part of the outer surface of the wall of the pipeline. The second set of measured data elements may be acquired by using a relatively fast, e.g. less accurate, measurement method such as magnetic flux leakage (MFL) measurements, on a relatively large part of the inner surface of the wall of the pipeline, for example nearly the entire inner surface of the wall of the pipeline. The second set of measured data elements may be acquired from at least a portion of the wall of the pipeline from which at least a portion of the first set of measured data elements was acquired. Thus, the at least portion of the first set of measured data elements and the second set of measured data elements are acquired from at least one and the same portion of the wall of the pipeline.

Figure 4A:
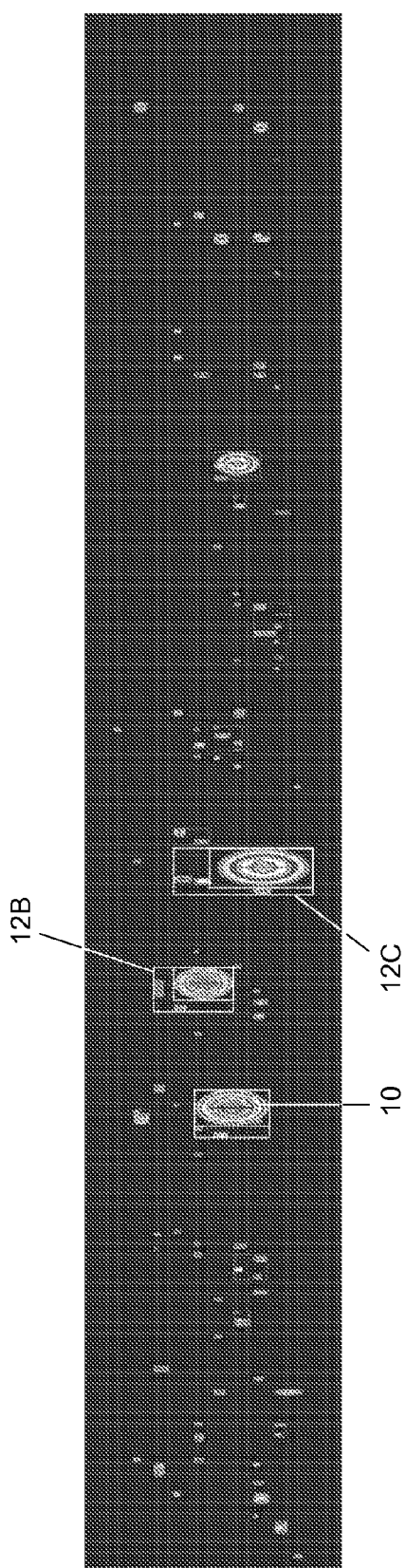
FIG. 4A shows an example of edge envelopes of a second set of measured data elements.
Figure 4B:
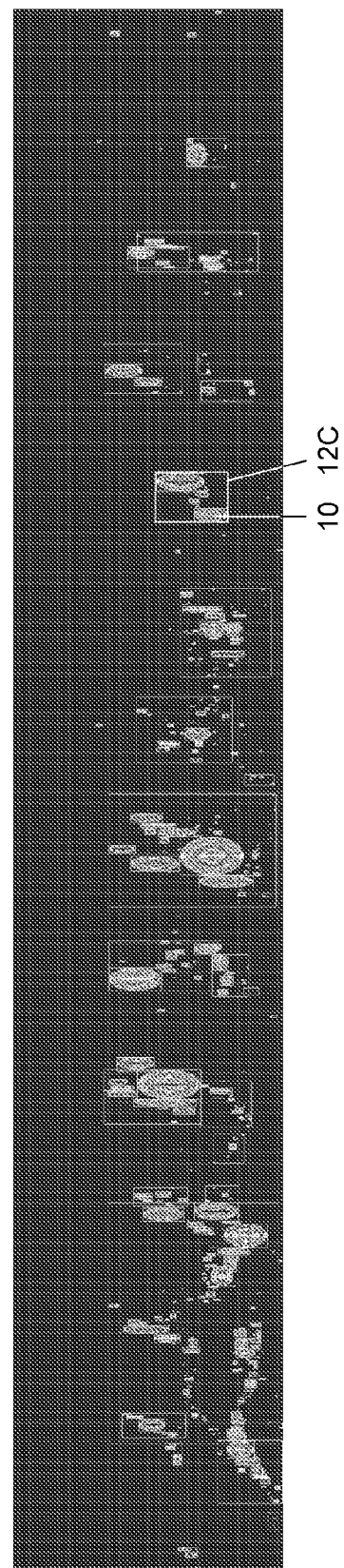
FIG. 4B shows an example of edge envelopes of a first set of measured data elements.

The third method may comprise defining a plurality of edge envelopes of anomalies of the first data set associated with the portion of the wall of the pipeline. This may e.g. be carried out in a similar way as defining the base edge envelope 12A of the first anomaly in the first method, or as defining the interaction edge envelope 12B and/or the further interaction edge envelope 12C in the second method. Thus, defining the plurality of edge envelopes may comprise defining interaction edge envelopes. Thus, the plurality of edge envelopes may comprise the first edge envelop, the second edge envelope, the third edge envelope, the fourth edge envelope, the fifth edge envelope, the sixth edge envelope, the seventh edge envelope, the eighth edge envelope, the common edge envelope, the further common edge envelope, and/or one or more other (interaction) edge envelopes. FIG. 4B shows an example of the edge envelopes 12 of the first set of measured data elements, in this example comprising base edge envelopes 12A, interaction edge envelopes 12B, and further interaction edge envelopes 12C, of the anomalies 10 of the first set of measured data elements.

Similarly, the third method may comprise defining a plurality of edge envelopes of anomalies of the second set of measured data elements associated with the portion of the wall of the pipeline. FIG. 4A shows an example of the edge envelopes 12 of the second set of measured data elements, in this example comprising base edge envelopes 12A, interaction edge envelopes 12B, and further interaction edge envelopes 12C, of the anomalies 10 of the second set of measured data elements.

The third method may further comprise comparing the plurality of edge envelopes of the anomalies of the first set of measured data elements with the plurality of the edge envelopes of the anomalies of the second set of measured data elements. Such comparing may comprise, more in general comparing at least one of a width of the edge envelopes, a length of the edge envelopes, a position of the edge envelopes, and a depth associated with the edge envelopes. The width W of an edge envelope may for example be measured along the first direction 2, and the length L of an edge envelope may for example be measured along the second direction 4 (see FIG. 1), or vice versa. A depth associated with an edge envelope may be dependent on a depth of the anomaly associated with that edge envelope. The depth associated with an edge envelope may e.g. be set proportional to, in particular equal to, a maximum depth of the anomaly associated with that edge envelope. More in general, statistical techniques that are known as such may be used during such comparing.

If said comparing yields differences between the edge envelopes of the first and second sets of measured data elements, the third method may further comprise adapting the edge envelopes of the second set of measured data elements. Such adapting may be based on said comparing, and may comprise shifting a position of the edge envelopes of the second set of measured data elements.

In a fourth embodiment of a method according to the invention (the fourth method), the third method can be further extended.

For example, in the fourth method the adapting may comprise redefining the edge envelopes 12 of the anomalies of the second set of measured data elements. For example, a further interaction edge envelope may be replaced by two or more interaction edge envelopes. For example, an interaction edge envelope may be replaced by two base edge envelopes. In this way, more in general, adapting may include reclustering of edge envelopes 12A, 12B, 12C.

Thus, the fourth method may comprise reclustering by redefining the edge envelopes of the second set of measured data by replacing at least two base edge envelopes of the second set of measured data by an interaction edge envelope of the second set of measured data that encloses the at least two base edge envelopes. Alternatively or additionally, the fourth method may comprise reclustering by redefining the edge envelopes of the second set of measured data by replacing an interaction edge envelope of the second set of measured data by at least two base edge envelopes of the second set of measured data that were, before replacing, enclosed by the interaction edge envelope of the second set of measured data elements.

The first and/or second set of measured data elements may have been acquired by means of an in-line inspection method of the pipeline. Such methods are known as such to the skilled person and may be performed by launching an in-line-inspection tool (also referred to as a 'pig') fitted with measurement sensors, e.g. laser profilometry sensors, magnetic flux leakage (MFL) sensors, ultrasonic measurement sensors, and/or electromagnetic acoustic transducers, that perform measurements as the tool travels through the pipeline. Such in-line inspection method are known as such so that a further description is deemed superfluous. A travel direction of the inspection tool through the pipeline when acquiring the first set of measured data elements may be opposite or similar to a travel direction of the inspection tool through the pipeline when acquiring the second set of measured data elements. In case of opposite direction, aligning as in the third method is especially valuable.

The invention is not limited to any embodiment herein described and, within the purview of the skilled person, modifications are possible which should be considered within the scope of the appended claims. For example, any embodiment described herein, in particular the third and/or fourth method, may comprise analysing and/or interpreting the second set of measured data elements after adapting based on comparing with the first set of measured data elements. Analysing and interpreting may be carried out to determine the condition of the pipeline. Subsequently, pipeline operators may devise a mitigation and, if necessary, repair plan to maintain safe operation of the pipeline. As another example, any method described herein with reference to the first, second and/or third anomaly, may be repeated and/or may be carried out for a plurality of anomalies. Hence, any method described herein for determining the edge of the first anomaly may be repeated and carried out for determining edges of a plurality of anomalies. As yet another example, any method described herein for the first, second and/or third edge envelope may be carried out for an interaction edge envelope and/or a further interaction edge envelope instead of the first, second and/or third edge envelope. Thus, in general, the first, second and/or third edge envelope may be formed by an interaction edge envelope and/or a further interaction edge envelope instead of the first, second and/or third edge envelope. Equally all kinematic inversions are considered inherently disclosed and to be within the scope of the present invention. Further aspects of the invention may comprise: a method of determining whether anomalies in a wall of a pipeline interact, comprising to the steps: —defining a base edge envelope of a first anomaly that encloses an edge of the first anomaly, wherein the base edge envelope of the first anomaly preferably is box-shaped, —defining a base edge envelope of a second anomaly that encloses an edge of the second anomaly, wherein the base edge envelope of the second anomaly preferably is box-shaped, —determining, based on the base edge envelope of the first anomaly and the base edge envelop of the second anomaly, and by using an interaction criterium, whether the first anomaly and the second anomaly interact; and/or may comprise: a method of aligning a first set of measured data elements with a second set of measured data elements, wherein at least a part of the first set of measured data elements and at least a part of the second set of measured data elements are acquired from one and the same portion of the wall of the pipeline, the method comprising the steps: —defining a plurality of edge envelopes of the anomalies of the first set of measured data element associated with the portion of the wall of the pipeline, —defining a plurality of edge envelopes of the anomalies of the second set of measured data elements associated with the portion of the wall of the pipeline, —comparing the plurality of the edge envelopes of the anomalies of the first set of measured data elements with the plurality of the edge envelopes of the anomalies of the second set of measured data elements, and —adapting the edge envelopes of the second set of measured data elements, based on said comparing. The use of expressions like: "preferably", "preferred", "in particular" etc. is not intended to limit the invention. Adjectives like 'first', 'second', 'third' etc. may be merely used for distinguishing between like elements without implying an order or limitation in number. Features which are not specifically or explicitly described or claimed may be additionally included in the structure according to the present invention without deviating from its scope.

The invention claimed is:

1. Method of determining a boundary of a first anomaly in a wall of a pipeline from a first set of data elements of the wall of the pipeline, an element of the first set comprising a first coordinate along a first direction along the wall, a second coordinate along a second direction along the wall that is different from the first direction, and a parameter indicative of a depth of the first anomaly, at a position along the wall indicated by the first and second coordinate, the method comprising the steps:
   a) determining, by evaluating the parameters of the data elements, a data element that is associated with a minimum or a maximum in a value of the parameter of the data element;
   b) comparing, for at least one data element present on a path along the wall which extends away from the data element found in step a), a value of the parameter of the at least one data element with a predetermined threshold;
   c) determining an initial edge data element for which, during comparing in step b), a value of the parameter of the initial edge data element has reached the threshold and a value in the parameter for an adjacent data element in the path along the wall has not reached the threshold, and wherein the boundary of the first anomaly comprises the initial edge data element;
   d) determining, by evaluating the parameter of at least one data element that is adjacent to the initial edge data element determined in step c), a next edge data element that is different from the initial edge data element determined in step c) and for which the value of the parameter has reached the threshold;
   e) determining further edge data elements by repeating step d) a plurality of times wherein each next edge data element that is determined in a step d) is different from previously determined edge data elements; and
   f) determining the boundary of the first anomaly by combining the first and second coordinates of the edge data elements determined in steps c)-e),
   wherein a non-transitory computer is used to carry out the method.

2. Method according to claim 1, wherein determining the data element that is associated with the minimum or the maximum in the value of the parameter comprises determining the data element that is associated with a minimum in the value of the parameter that is smaller than the threshold, or wherein determining the data element that is associated with the minimum or the maximum in the value of the parameter comprises determining the data element that is associated with a maximum in the value of the parameter that is larger than the threshold.

3. Method according to claim 1, wherein the boundary of the first anomaly determined in step f) forms an edge path around the data element that is associated with the minimum or the maximum in the value of the parameter.

4. Method according to claim 3, wherein the edge path encloses anomaly data elements, and wherein, if the minimum or maximum in the value of the parameter is associated with the minimum in the value of the parameter the anomaly data elements have a value of the parameter that is smaller than the threshold, or wherein, if the minimum or maximum in the value of the parameter is associated with the maximum in the value of the parameter the anomaly data elements have a value of the parameter that is larger than the threshold.

5. Method according to claim 1, wherein step e) is repeated until one of the further edge data elements is adjacent to the initial edge data element determined in step c).

6. Method according to claim 1, wherein the path along the wall extends in a direction parallel with the first direction or the second direction.

7. Method according to claim 1, further comprising the step:
   g) defining a box-shaped edge envelope of the first anomaly that extends via at least one of the edge data elements of the first anomaly, and that encloses the boundary of the first anomaly.

8. Method according to claim 1, comprising the steps:
   h) repeating steps a)-f) for determining a boundary of a second anomaly that is different from the first anomaly;
   i) determining, based on the boundary of the first anomaly and the boundary of the second anomaly whether the first anomaly and the second anomaly interact.

9. Method according to claim 8, wherein determining in step i) is based on a box-shaped edge envelope of the first anomaly and the boundary of the second anomaly.

10. Method according to claim 8, including the step:
   j) defining a box-shaped edge envelope of the second anomaly that extends via at least one of the edge data elements of the second anomaly, and that encloses the boundary of the second anomaly, wherein determining in step i) is based on the box-shaped edge envelope of the first anomaly and the box-shaped edge envelope of the second anomaly.

11. Method according to claim 10, wherein determining in step i) whether the first anomaly and the second anomaly interact comprises enlarging the box-shaped edge envelope of the first anomaly to obtain an enlarged box-shaped edge envelope and further comprises determining whether the enlarged box-shaped edge envelope overlaps, overlays and/or crosses the box-shaped edge envelope of the second anomaly.

12. Method according to claim 8, wherein a step k) is carried out if in step i) it is determined that the first anomaly and the second anomaly interact, wherein step k) comprises:
   defining an interaction edge envelope that extends via at least one of the edge data elements of the first and second anomaly, and that encloses edge a boundary of the first and the second anomaly.

13. Method according to claim 1, comprising the steps:
   repeating steps a)-f) for determining a boundary of a second anomaly that is different from the first anomaly;
   l) repeating steps a)-f) for defining a boundary of a third anomaly that is different from the first anomaly and the second anomaly; and
   m) determining, based on the boundary of the first anomaly, the boundary of the second anomaly, and the boundary of the third anomaly whether the first anomaly and/or the second anomaly interact with the third anomaly.

14. Method according to claim 13, further comprising defining an interaction edge envelope that extends via at least one of the edge data elements of the first and second anomaly, and that encloses a boundary of the first and the second anomaly, wherein determining in step m) is based on the interaction edge envelope and the boundary of the third anomaly.

15. Method according to claim 14, including the step:

n) defining a box-shaped edge envelope of the third anomaly that extends via at least one of the edge data elements of the third anomaly, and that encloses the boundary of the third anomaly, wherein determining in step m) is based on the interaction edge envelope and the box-shaped edge envelope of the third anomaly.

16. Method according to claim 15, wherein determining in step m) whether the first anomaly and/or the second anomaly interact with the third anomaly comprises enlarging the interaction edge envelope to obtain an enlarged interaction edge envelope and further comprises determining whether the enlarged interaction edge envelope overlaps, overlays and/or crosses the box-shaped edge envelope of the third anomaly.

17. Method according to claim 1, wherein the first set of data elements is acquired by means of laser profilometry.

18. Method according to claim 13, wherein the first anomaly, the second anomaly, and the third anomaly are located on an inner or outer surface of the wall of the pipeline.

19. Method according to claim 7, comprising aligning the first set of data elements with a second set of data elements, wherein at least a part of the first set of data elements and at least a part of the second set of data elements are acquired from one and the same portion of the wall of the pipeline, the method comprising the steps:

o) defining a plurality of edge envelopes of the anomalies of the first set of data elements associated with the portion of the wall of the pipeline, which are defined similarly to defining the edge envelope of the first anomaly;

p) defining a plurality of edge envelopes of the anomalies of the second set of data elements associated with the portion of the wall of the pipeline;

q) comparing the plurality of the edge envelopes of the anomalies of the first set of data elements with the plurality of the edge envelopes of the anomalies of the second set of data elements; and r) adapting the edge envelopes of the second set of data elements, based on the comparing of step q).

20. Method according to claim 19, wherein adapting in step r) comprises shifting a position of the edge envelopes of the second set of data elements.

21. Method according to claim 19, wherein adapting in step r) includes redefining the edge envelopes of the anomalies of the second set of data elements.

22. Method according to claim 19, wherein comparing edge envelopes in step q) comprises comparing at least one of a width of the edge envelopes, a length of the edge envelopes, a position of the edge envelopes, and a depth associated with the edge envelopes.

23. Method according to claim 19, wherein the first and/or second set of data elements is acquired by means of an in-line inspection method of the pipeline.

24. Method according to claim 19, wherein the second set of data elements is acquired by means of a magnetic flux leakage (MFL) inspection, by ultrasonic inspection, and/or by electromagnetic-acoustic inspection of the pipeline.

25. Method of determining whether a first anomaly and a second anomaly in a wall of a pipeline interact, based on boundaries of the first and second anomaly that are determined from a first set of measured data elements of the wall of the pipeline, the boundaries enclosing anomaly data elements associated with the first or second anomaly, the method comprising the steps:

s) providing a box-shaped edge envelope of the first anomaly that encloses the boundary of the first anomaly;

t) providing a box-shaped edge envelope of the second anomaly that encloses the boundary of the second anomaly;

u) determining, based on the box-shaped edge envelope of the first anomaly and the box-shaped edge envelope of the second anomaly whether the first anomaly and the second anomaly interact.

26. Method according to claim 25, wherein the boundary of the first anomaly forms an edge path around the anomaly data elements of the first anomaly and/or the boundary of the second anomaly forms an edge path around the anomaly data elements of the second anomaly.

27. Method according to claim 25, wherein determining in step u) whether the first anomaly and the second anomaly interact comprises enlarging the edge envelope of the first anomaly to obtain an enlarged edge envelope and further comprises determining whether the enlarged edge envelope overlaps, overlays and/or crosses the edge envelope of the second anomaly.

28. Method of aligning a first set of measured data elements with a second set of measured data elements of a wall of the pipeline, wherein at least a part of the first set of measured data elements and at least a part of the second set of measured data elements are acquired from one and the same portion of the wall of the pipeline, wherein boundaries of anomalies are provided that are determined from the first and second set of measured data elements, the boundaries enclosing anomaly data elements, the method comprising the steps:

v) providing a plurality of edge envelopes of the anomalies of the first set of measured data elements associated with the portion of the wall of the pipeline;

w) providing a plurality of edge envelopes of the anomalies of the second set of measured data elements associated with the portion of the wall of the pipeline;

x) comparing the plurality of the edge envelopes of the anomalies of the first set of measured data elements with the plurality of the edge envelopes of the anomalies of the second set of measured data elements; and y) adapting the edge envelopes of the second set of measured data elements, based on the comparing of step x)

wherein a non-transitory computer is used to carry out the method.

29. Method according to claim 28, wherein adapting in step y) comprises shifting a position of the edge envelopes of the second set of measured data elements.

30. Method according to claim 28, wherein adapting in step y) includes redefining the edge envelopes of the anomalies of the second set of measured data elements.

31. Method according to claim 28, wherein comparing edge envelopes in step q) comprises comparing at least one of a width of the edge envelopes, a length of the edge envelopes, a position of the edge envelopes, and a depth associated with the edge envelopes.

32. Method according to claim 25, wherein the first and/or second set of measured data elements is acquired by means of an in-line inspection method of the pipeline.

33. Method according to claim 25, wherein the first set of measured data elements is acquired by means of laser profilometry.

34. Method according to claim 28, wherein the second set of measured data elements is acquired by means of a magnetic flux leakage (MFL) inspection, by ultrasonic inspection, and/or by electromagnetic-acoustic inspection of the pipeline.

35. Method according to claim 25, wherein the anomalies are located on an inner or outer surface of the wall of the pipeline.

36. Computer program product including computer code portions arranged for performing, when run on a programmable apparatus, the steps of the method according to claim 1.

37. Non-transitory data carrier comprising software code portions arranged for performing, when run on a programmable apparatus, the steps of the method according to claim 1.

38. A non-transitory computer readable medium containing executable instructions that when executed perform a method of determining a boundary of a first anomaly in a wall of a pipeline from a first set of data elements of the wall of the pipeline, an element of the first set comprising a first coordinate along a first direction along the wall, a second coordinate along a second direction along the wall that is different from the first direction, and a parameter indicative of a depth of the first anomaly, at a position along the wall indicated by the first and second coordinate, the method comprising the steps:
 a) determining, by evaluating the parameters of the data elements, a data element that is associated with a minimum or a maximum in a value of the parameter of the data element;
 b) comparing, for at least one data element present on a path along the wall which extends away from the data element found in step a), a value of the parameter of the at least one data element with a predetermined threshold;
 c) determining an initial edge data element for which, during comparing in step b), a value of the parameter of the initial edge data element has reached the threshold and a value in the parameter for an adjacent data element in the path along the wall has not reached the threshold, and wherein the boundary of the first anomaly comprises the initial edge data element;
 d) determining, by evaluating the parameter of at least one data element that is adjacent to the initial edge data element determined in step c), a next edge data element that is different from the initial edge data element determined in step c) and for which the value of the parameter has reached the threshold;
 e) determining further edge data elements by repeating step d) a plurality of times wherein each next edge data element that is determined in a step d) is different from previously determined edge data elements; and
 f) determining the boundary of the first anomaly by combining the first and second coordinates of the edge data elements determined in steps c)-e), 39. A non-transitory computer readable medium containing executable instructions that when executed perform a method of aligning a first set of measured data elements with a second set of measured data elements of a wall of the pipeline, wherein at least a part of the first set of measured data elements and at least a part of the second set of measured data elements are acquired from one and the same portion of the wall of the pipeline, wherein boundaries of anomalies are provided that are determined from the first and second set of measured data elements, the boundaries enclosing anomaly data elements, the method comprising the steps:
 v) providing a plurality of edge envelopes of the anomalies of the first set of measured data elements associated with the portion of the wall of the pipeline;
 w) providing a plurality of edge envelopes of the anomalies of the second set of measured data elements associated with the portion of the wall of the pipeline;
 x) comparing the plurality of the edge envelopes of the anomalies of the first set of measured data elements with the plurality of the edge envelopes of the anomalies of the second set of measured data elements; and
 y) adapting the edge envelopes of the second set of measured data elements, based on the comparing of step x).

* * * * *